(12) United States Patent
Javors

(10) Patent No.: US 11,648,126 B1
(45) Date of Patent: May 16, 2023

(54) METHOD AND SYSTEM FOR FEMORAL CONDYLAR RESECTION ARTHROPLASTY OF THE KNEE

(71) Applicant: Jonathan R. Javors, Valparaiso, IN (US)

(72) Inventor: Jonathan R. Javors, Valparaiso, IN (US)

( * ) Notice: Subject to any disclaimer, the term of this patent is extended or adjusted under 35 U.S.C. 154(b) by 198 days.

(21) Appl. No.: 16/784,029

(22) Filed: Feb. 6, 2020

Related U.S. Application Data

(63) Continuation-in-part of application No. 15/595,053, filed on May 15, 2017, now Pat. No. 10,918,396, which is a continuation-in-part of application No. 15/464,241, filed on Mar. 20, 2017, now Pat. No. 10,918,399, which is a continuation-in-part of application No. 15/427,016, filed on Feb. 7, 2017, now Pat. No. 10,426,504.

(51) Int. Cl.
*A61F 2/38* (2006.01)

(52) U.S. Cl.
CPC ............ *A61F 2/3859* (2013.01); *A61F 2/385* (2013.01); *A61F 2002/3863* (2013.01); *A61F 2310/00011* (2013.01)

(58) Field of Classification Search
CPC . A61F 2/385; A61F 2/3859; A61F 2002/3863
See application file for complete search history.

(56) References Cited

U.S. PATENT DOCUMENTS

| | | | | |
|---|---|---|---|---|
| 5,464,406 A | * | 11/1995 | Ritter | A61B 17/921 |
| | | | | 606/86 R |
| 5,645,602 A | * | 7/1997 | Albrektsson | A61F 2/3859 |
| | | | | 623/23.11 |
| 9,168,155 B2 | * | 10/2015 | Earl | A61F 2/3859 |
| 2003/0055501 A1 | * | 3/2003 | Fell | A61F 2/3872 |
| | | | | 623/14.12 |

* cited by examiner

*Primary Examiner* — Christopher D. Prone
(74) *Attorney, Agent, or Firm* — Charles T. Riggs, Jr.

(57) ABSTRACT

A method and system for femoral condylar resection arthroplasty (FCRA) of the knee, which preserves the undamaged meniscus, whether by arthroscopy or arthrotomy, and only replaces the damaged area of the femoral condyle. In one embodiment, both the distal and posterior femoral condyle are replaced with a two piece femoral two-piece distal and posterior femoral condyle component. This two piece component has a metal piece and a plastic piece removably attached in a tongue and groove arrangement. This arrangement allows the plastic piece to be removed when converting the FCRA into a unicompartmental arthroplasty.

3 Claims, 13 Drawing Sheets

FIGURE 2A
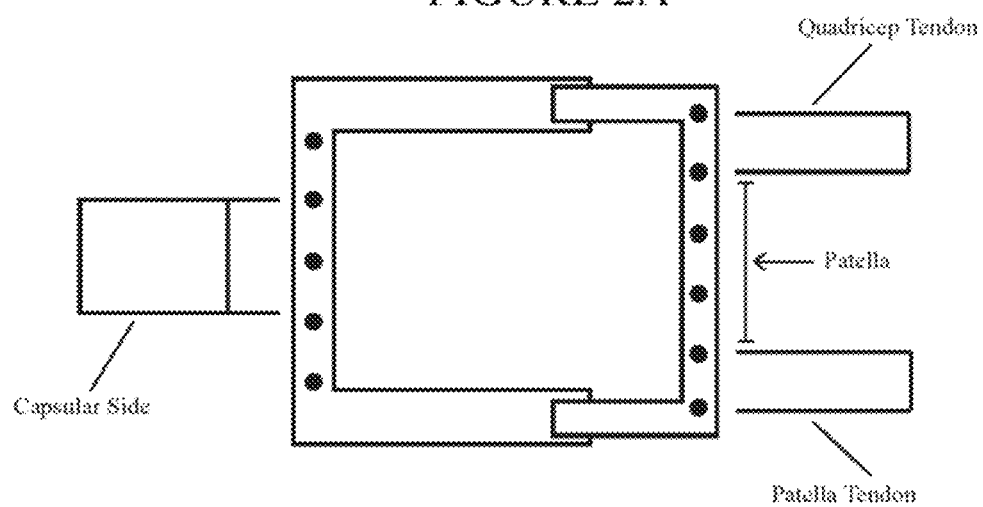
FIGURE 2B
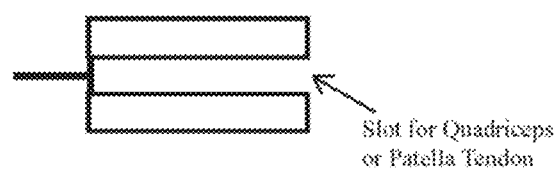
FIGURE 2C

SIDE VIEW

TOP VIEW

FRONT VIEW

SIDE VIEW

FIGURE 5A
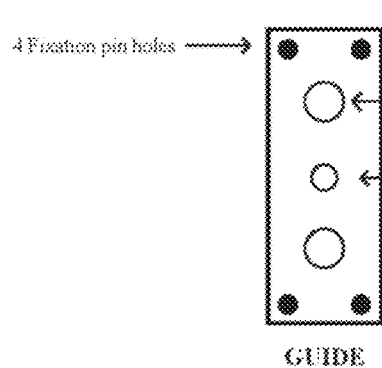
FIGURE 5B
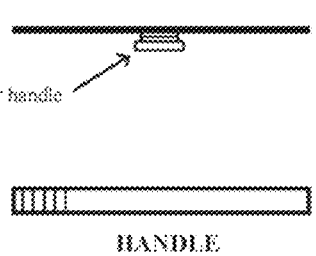
FIGURE 5C
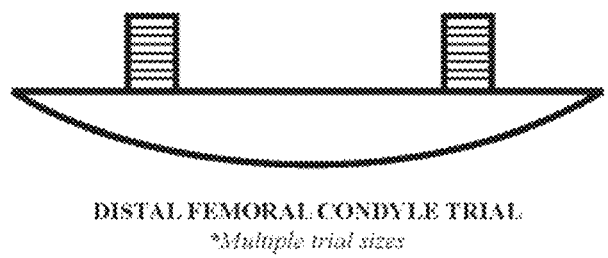
FIGURE 5D

DISTAL AND POSTERIOR FEMORAL CONDYLE TRIAL

FIGURE 7A
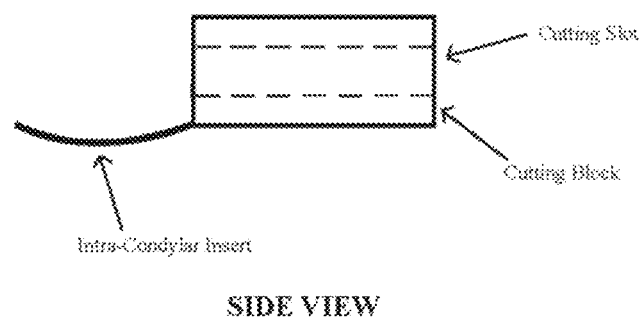
SIDE VIEW
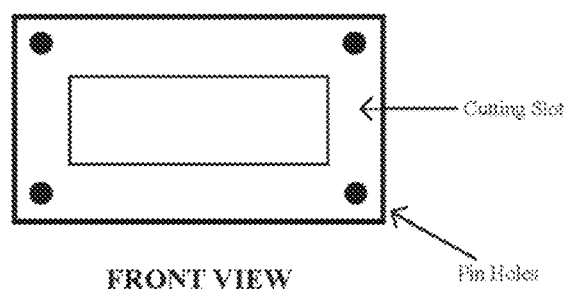
FRONT VIEW
FIGURE 7B

METHOD AND SYSTEM FOR FEMORAL CONDYLAR RESECTION ARTHROPLASTY OF THE KNEE

This application is a continuation in part of U.S. patent application Ser. No. 15/595,053 filed May 15, 2017, now U.S. Pat. No. 10,918,396 issued Feb. 16, 2021, which is a continuation in part of U.S. patent application Ser. No. 15/464,241 filed Mar. 20, 2017, now U.S. Pat. No. 10,918,399 issued Feb. 16, 2021, which is a continuation in part of U.S. patent application Ser. No. 15/427,016 filed Feb. 7, 2019, now U.S. Pat. No. 10,426,504 issued Oct. 1, 2019.

TECHNICAL FIELD

The exemplary teachings herein pertain to methods, systems, components and/or devices for femoral condylar resection arthoplasty (FCRA) of the knee.

BACKGROUND

Since Sir John Charnley pioneered the design and implementation of the total hip arthroplasty in the mid-1960s, joint replacement surgeons and orthopedic product companies have been striving to improve on the original design, often in collaboration. These improvements have been focused on the following goals:

i) Improvement of patient function
ii) Ease of insertion, through improved instrument design and surgical approach
iii) Reproduction of beneficial results, both from the patient and surgeon standpoints
iv) Longevity of the product
v) Smaller incisions
vi) Faster recovery
vii) Shorter operating time
viii) Multi-modal pain control parameters Over the last fifty years, significant strides have been made in all of these goals. Newer products with improved materials have increased component longevity. Minimally invasive techniques, with multi-modal pain control, standardization of physical therapy protocols, and improved instrument design have all improved patient function and shortened recovery time. Procedures being performed more frequently by surgeons better versed in joint replacement surgery have led to more beneficially reproducible results.

One of the primary goals of all joint replacement arthroplasty techniques and designs is to remove as little bone as possible to accomplish the above goals. Always in the back of every joint replacement surgeon's mind is the fact that if the patient lives long enough, of if they put undue stress across the joint, whether due to being too active, weight gain, or other factors, the prosthesis will fail. The smaller amount of bone removed at the time of the primary arthroplasty, the less invasive revision necessary.

Unicompartmental arthroplasty of the knee has been part of the joint replacement surgeon's armamentarium for over 35 years. Commonly, only one of the three compartments in the knee has damage and is symptomatic. The other two are normal. The unicompartmental arthroplasty allows for the removal of the damaged compartment but preserves the patient's normal and native undamaged compartments.

The standard design of the traditional unicompartmental knee arthroplasty (when replacing the medial or lateral compartments) is to replace the distal and posterior condyles of the femur and the articular surface of the tibial plateau of the involved compartment. The meniscus is removed. Often there is damage to the distal femoral weight bearing surface, yet the posterior femoral condyle and the tibial plateau articular surfaces are unaffected.

The following prior art references relate to and/or discuss one or more of the above described issues, and are each herein fully incorporated by reference: U.S. Patent Application Publication Nos. 2007/0032876 A1 entitled Knee Joint Prosthesis, published on Feb. 8, 2007, and 200810132895 A1 entitled Instruments and Method for Arthroscopic Arthroplasty of the Knee, published on Jun. 5, 2008, both by inventor Ron Clark of Valparasio, Ind.

SUMMARY

One or more methods, systems, designs, instruments, implements, components and/or devices for femoral condylar resection arthroplasty (FCRA) of the knee are disclosed. In a preferred embodiment, only the damaged femoral condyle of the knee (medial or lateral; distal and/or posterior, depending on the extent of damage) is replaced. By doing so, the method and system maintains the meniscus and corresponding tibial plateau, while replacing only the damaged surface of the femoral condyle and preserves normal tissue of the meniscus and tibial hyaline cartilage. This would be very beneficial in younger and more active patients. The method and system does not preclude a "traditional" uni-compartmental arthroplasty at some point in the future should that become necessary. The method and system can be performed with limited exposure, post arthroscopy for correction of other intra-articular knee pathology. The surgical time and recovery would be shorter because of the less invasive nature of the procedure.

The one or more methods, systems, designs, instruments, implements, components and/or devices incorporate the following characteristics and/or features:

1) Preserves the undamaged part of the meniscus. All current unicompartmental arthroplasty techniques sacrifice the meniscus. In the procedures disclosed herein, only the torn part of the meniscus is removed in the first part of the process (surgical procedure) via the arthroscope.

2) Only replaces the damaged area of the femoral condyle (distal femoral condyle or both distal and posterior femoral condyle). Whether to replace the distal and/or the posterior femoral condyle is anticipated through careful review of the pre-op MRI, but confirmed at arthroscopy. If there is significant damage to the tibial plateau as seen at arthroscopy, in the pre-operative MRI, or at the time of arthrotomy, then a traditional unicompartmental arthroplasty is performed.

3) While either plastic or metal material for the components may be used, preferably plastic components are used, as plastic articulating on the hyaline cartilage tibial plateau will mimic nature better than metal.

4) Once the arthroscopic procedure is finished, the surgeon will than make a small (2-3 inch) incision, use the box retractor, slide in the intra-compartmental (IC) insert, place on the femoral cutting jig, fix it with pins, make the appropriate distal femoral cut, and cement in the component. If the posterior is to be replaced, a chamfer and posterior cut will be made, using existing cutting blocks.

5) The disclosed procedures may be performed by arthroscopic surgeons, in addition to joint arthroplasty surgeons.

The presently disclosure methods, systems, designs and instruments for femoral condylar resection arthroplasty provide the joint replacement surgeon and/or arthroscopic surgeon two primary options when performing femoral condylar replacement of either the medial or lateral compartments of the knee: 1) Replacement of the distal femoral condyle only, when the posterior femoral condyle and the tibial articular surfaces are both normal. This also allows for the preservation of stable medial meniscal tissue; or 2) Replacement of the entire femoral condyle, both distal and posterior.

Additional advantages and novel features will be set forth in part in the description which follows, and in part will become apparent to those skilled in the art upon examination of the following and the accompanying drawings or may be learned by production and/or operation of the teachings herein.

BRIEF DESCRIPTION OF THE DRAWINGS

The drawing figures depict one or more implementations in accordance with the present teachings, by way of example only, not by way of limitation. In the drawing figures, like reference numerals refer to the same or similar elements.

FIG. 2A is a schematic diagram of a box retractor used in the method(s) and system(s) of present disclosure.

FIG. 2B is a schematic diagram illustrating an anterior view of the box retractor of FIG. 2A.

FIG. 2C is a schematic diagram illustrating the tendon slots of the box retractor of FIG. 2A.

FIGS. 5A-5D are schematic diagrams of trial components used in the method(s) and system(s) of present disclosure, with FIG. 5A depicting a front view of a guide, FIG. 5B depicting a side view of a guide, FIG. 5C depicting a handle, and FIG. 5D depicting a distal femoral condyle trial.

FIG. 7A is a schematic diagram depicting a side view of a combined, one-piece Intra-condylar insert and distal femoral cutting block.

FIG. 7B is a schematic diagram depicting a front view of a combined, one-piece Intra-condylar insert and distal femoral cutting block.

DETAILED DESCRIPTION

The following description refers to numerous specific details which are set forth by way of examples to provide a thorough understanding of the relevant method(s) and system(s) disclosed herein. It should be apparent to those skilled in the art that the present disclosure may be practiced without such details. In other instances, well known methods, procedures, components, instruments, implements and/or devices have been described at a relatively high-level, without detail, in order to avoid unnecessarily obscuring aspects of the present disclosure.

Figure 1:
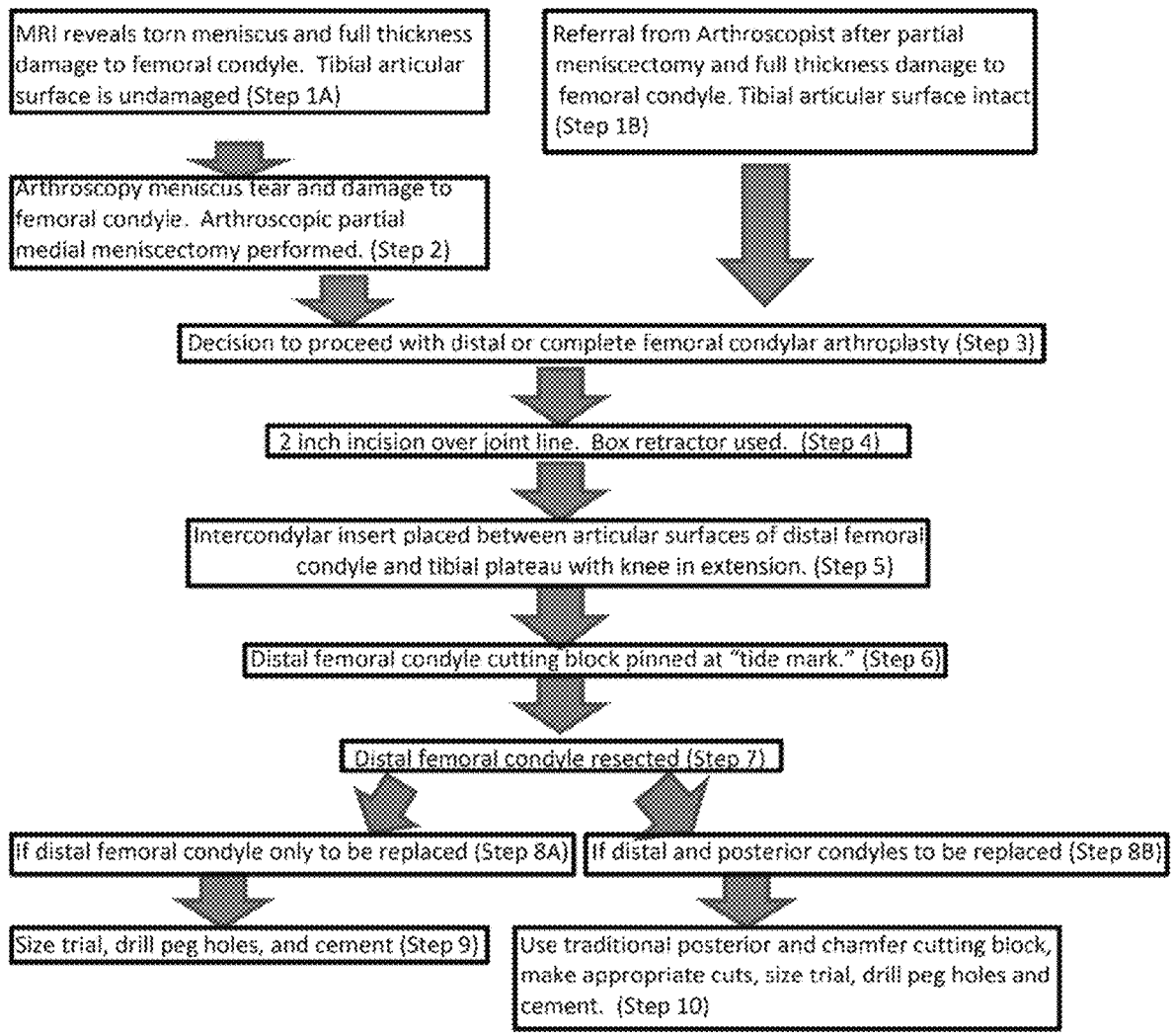
FIG. 1 is a flow chart illustrating the procedure(s) according to the present disclosure.
Figure 3A:
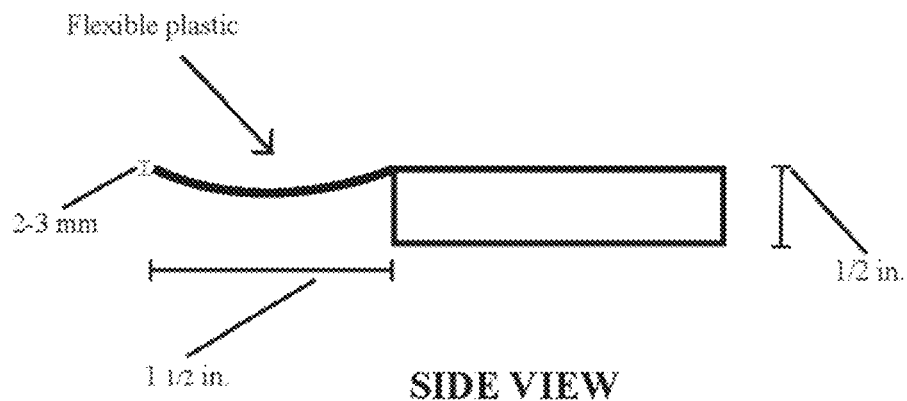
FIG. 3A is a schematic diagram depicting a side view of an intercompartmental (IC) insert used in the method(s) and system(s) of present disclosure.
Figure 3B:
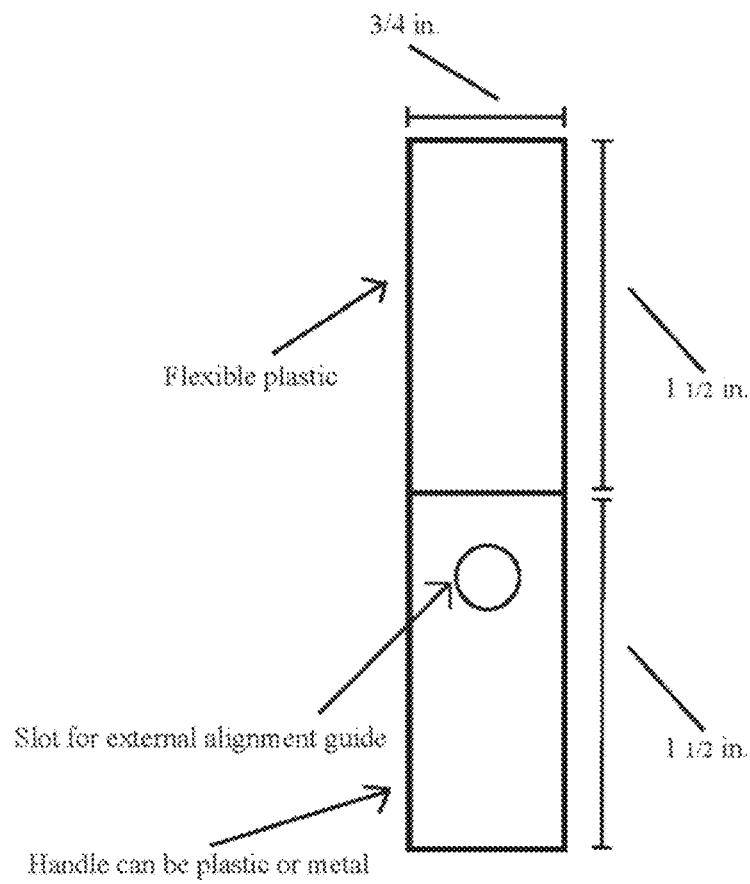
FIG. 3B is a schematic diagram depicting a top view of the intercompartmental (IC) insert of FIG. 3A.
Figure 4A:
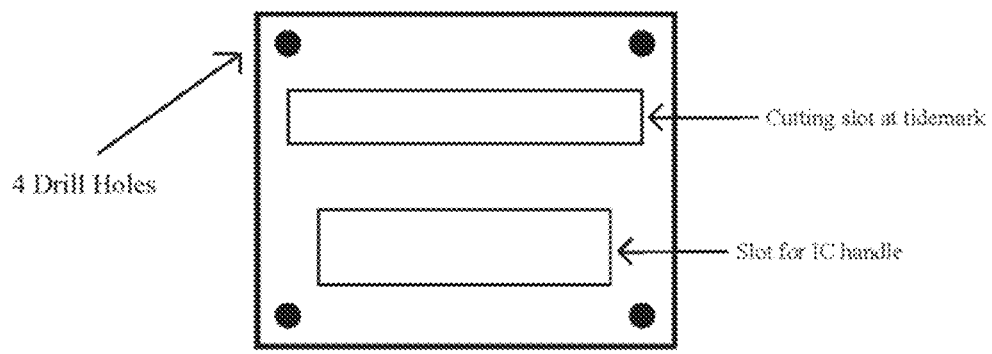
FIG. 4A is a schematic diagram depicting a front view of a cutting block used in the method(s) and system(s) of present disclosure.
Figure 4B:
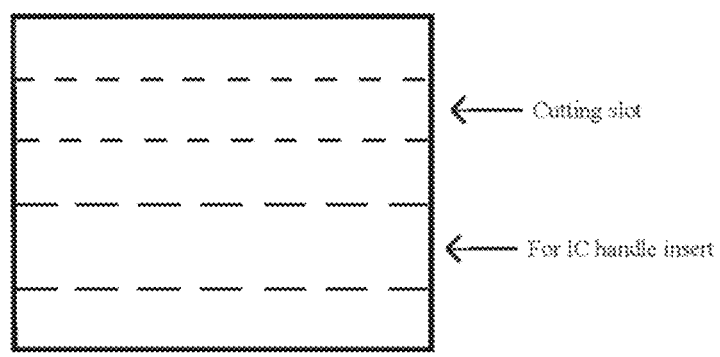
FIG. 4B is a schematic diagram depicting a side view of the cutting block of FIG. 4A.

FIG. 1 is flow chart illustrating the method(s) for the present disclosure for femoral condylar resection arthroplasty of the knee, with reference to the component(s) used during the method(s). Prior to a decision to proceed with distal or complete femoral condylar arthroplasty (FIG. 1, Step 3), an evaluation of a patient's knee must be undertaken (FIG. 1, Step 1A and/or Step 2), or a referral from an Arthroscopist is made (FIG. 1, Step 1B). Once the decision to proceed is made, the method includes the following steps: Step 4—an approximately two inch incision is made over joint line. As is well understood by one of ordinary skill in the art, the joint line of the knee refers to the anatomic interval between the distal femoral condyle and the proximal tibial plateau. These two anatomic areas comprise the knee joint. The box retractor of FIGS. 2A-2C is used. Step 5—the intercondylar insert of FIGS. 3A-3B is placed between articular surfaces of distal femoral condyle and tibial plateau with knee in extension. Step 6—the distal femoral condyle cutting block of FIGS. 4A-4B is pinned at "tide mark." Step 7—the distal femoral condyle resected. Step 8A—if the distal femoral condyle only to be replaced, perform Step 9: size trial, drill peg holes and cement using the trial components of FIGS. 5A-5D. Step 8B—if distal and posterior condyles to be replaced, perform Step 10: use traditional posterior and chamfer cutting block, make appropriate cuts, size trial, drill peg holes and cement using the trial components of FIGS. 5A-5C and 6.

FIGS. 3A and 3B illustrate the intra-compartmental insert (IC Insert). This insert has a curvilinear, pliable plastic surface that will be used for FCRA procedure. The joint replacement surgeon will use his or her preferred system for a traditional unicompartmental replacement. It is 1.5 cm wide. The curvilinear plastic component will be placed in between the tibial and femoral articular surfaces. The handle of the IC Insert will be hard plastic or metal and will contain a hole for placement of the external alignment guide.

FIGS. 4A-4B illustrate the distal femoral cutting block. This block will be attached to the IC Insert. Preferably, there will be neutral cutting slot. By slight angulation of the cutting block, e.g., 1 degree, 2 degree, or 3 degree superior slope, more or less of the distal condyle can be removed. This will allow a slight increased coverage if the distal femoral condyle wear extends slightly into the posterior condyle. However, unless otherwise determined, a neutral cut should be made. An alternate distal femoral cutting block is disclosed in FIGS. 4C-4D, and includes one or more guidewire slot(s) (two shown) through which one or more guidewire(s) can be placed to help line up the bone cut, as discussed in more detail below.

FIGS. 2A-2C illustrate the box retractor. This box retractor is a retractor designed specifically for the FCRA procedure. Since the incision only needs to expose the most inferior aspect of the distal femur and most superior aspect of the tibia, it may be relatively small. However, the patella, the patellar and quadriceps tendon, and the opposite capsular structures must be retracted to allow placement of the instruments and allow visualization of the bone cuts, trial sizing, and then placement of the definitive component. There are four right angle blades (two for medial structures and two for lateral structures), which may be either metal or hard plastic (if necessary to place the retractor under the patella itself). The blades come in two depths, shallow and deep. The metal lattice support is movable superior/inferior and medial/lateral to allow for adequate exposure. This also keeps the retractor in place while flexing and extending the knee.

FIG. 5D illustrates the distal femoral condyle replacement component or trial. There are three possibilities for the distal femoral condyle replacement:

1) Metal component with at least two pegs cemented into the distal femoral condyle;

2) Plastic component with at least two pegs cemented into the distal femoral condyle; and 3) Metal back component with at least two pegs cemented into the distal femoral condyle, with snap on plastic liners of various thicknesses.

Whether the distal femoral condyle is replaced, or both the distal and posterior femoral condyles are replaced, the trial components are made of plastic.

If the implanted metal component is used, this is a single component. If the implanted polyethylene is used, this is a single component.

Figure 8:
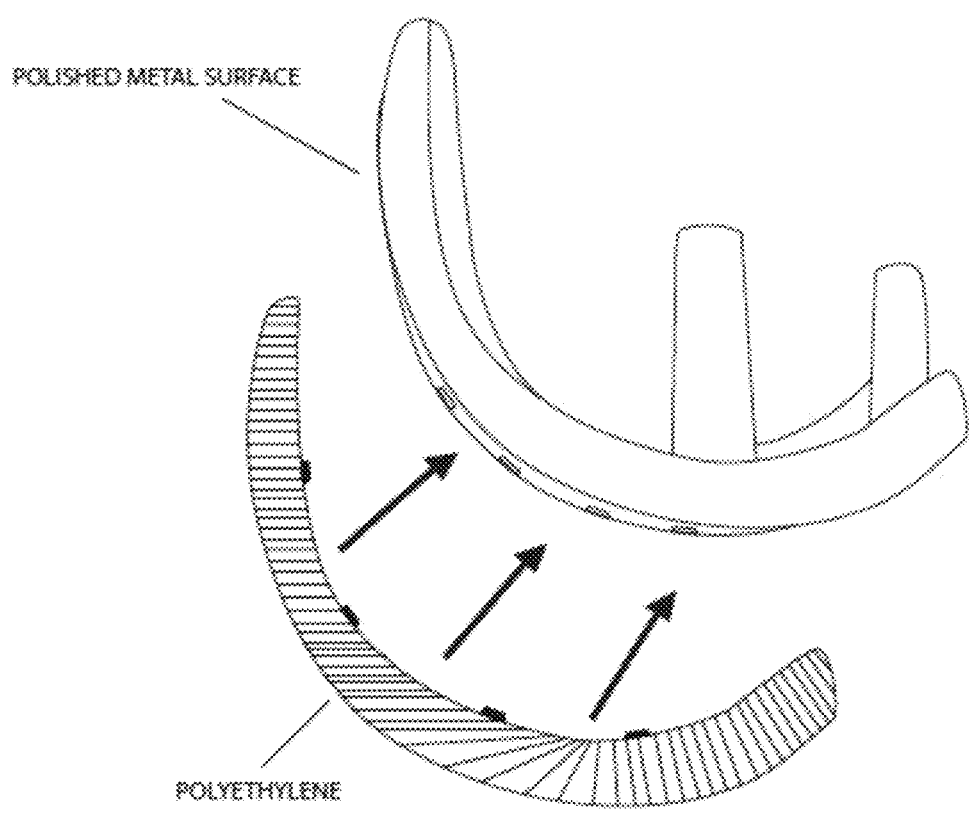
FIG. 8 is a schematic diagram depicting a two-piece implant distal femoral condyle, illustrating the two pieces prior to attachment.

However, if the metal backed component (cemented into bone) is used with the polyethylene component that will articulate with the tibial plateau hyaline cartilage and the remaining meniscus, this is a two piece femoral condyle implanted component as illustrated in FIG. 8. This two piece component is used only when both the distal and posterior femoral condyle is replaced, not when the distal femoral condyle only is being replaced.

Figure 9:
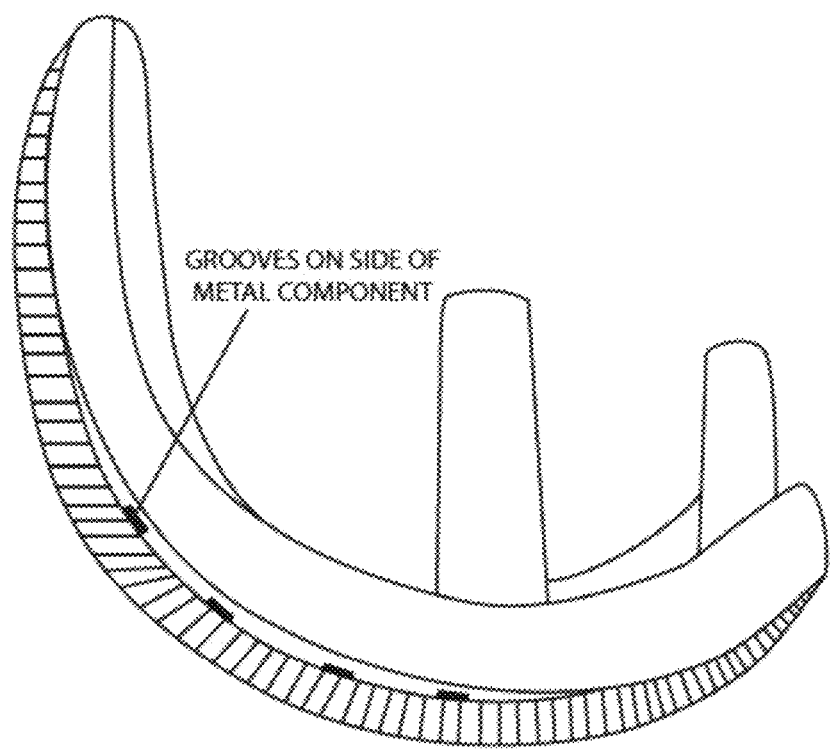
FIG. 9 is a schematic diagram depicting a two-piece implant distal femoral condyle, illustrating the two pieces attached together.

In the embodiment illustrated in FIG. 8, the surface of the metal component in the two-piece implant includes structural features, preferably but not limited to grooves, for attachment of the polyethylene surface. The surface that the polyethylene will affix to, can be polished and be made of same metal as the current femoral condylar components of traditional unicompartmental systems (e.g. chromium cobalt, oxinium, titanium). However, the metal component will possess grooves that will allow the polyethylene surface to be affixed to it in a tongue and groove type fashion, as illustrated in FIG. 9.

Figure 10:
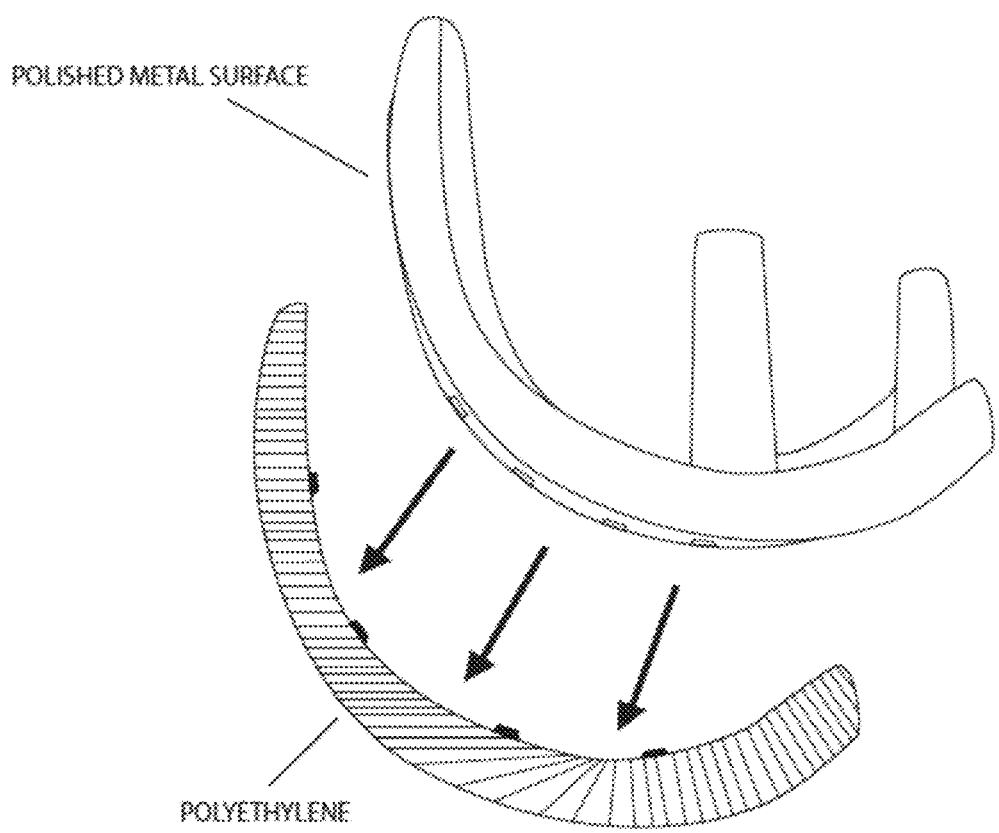
FIG. 10 is a schematic diagram depicting a two-piece implant distal femoral condyle, illustrating the two pieces after being separated or detached.

At the time a revision from the FCRA to a traditional unicompartment arthroplasty may become necessary, a small osteotome or freer tool can be used to remove or separate the original polyethylene component from the metal component, as shown in FIG. 10. This will then allow the remaining metal component from the original FCRA to be used, obviating the need to replace the femoral component. Only the tibial articular surface will need to be replaced.

The plastic component is preferably formed as one solid piece, and includes structural features, preferably but not limited to ridges, for attachment of the metal surface. This piece, by way of the tongue-in-groove arrangement, will snap-fit into the metal component, i.e., the ridges into the grooves. The polished metal surface will be cemented into the bone, after the trial determines the proper size. The polyethylene component will then be snapped fitted into the metal component, (FIGS. 8 and 9). If/when the FCRA then needs to converted into a unicompartmental arthroplasty, advantageously, only the polyethylene component is removed. It is unsnapped from the cemented metal component (FIG. 10). Advantageously, the surgeon does not have to remove the metal component from the bone, which to do so would entail removing more bone. Thus, femoral condyle bone is preserved. This also will decrease the surgical time, because the metal component will not have to be removed. To convert to a unicompartmental arthroplasty, only the tibial metal component with its polyethylene component will have to be put in. The femoral component is already in the place, i.e., the polished metal component that was cemented as part of the original FCRA.

Figure 11:
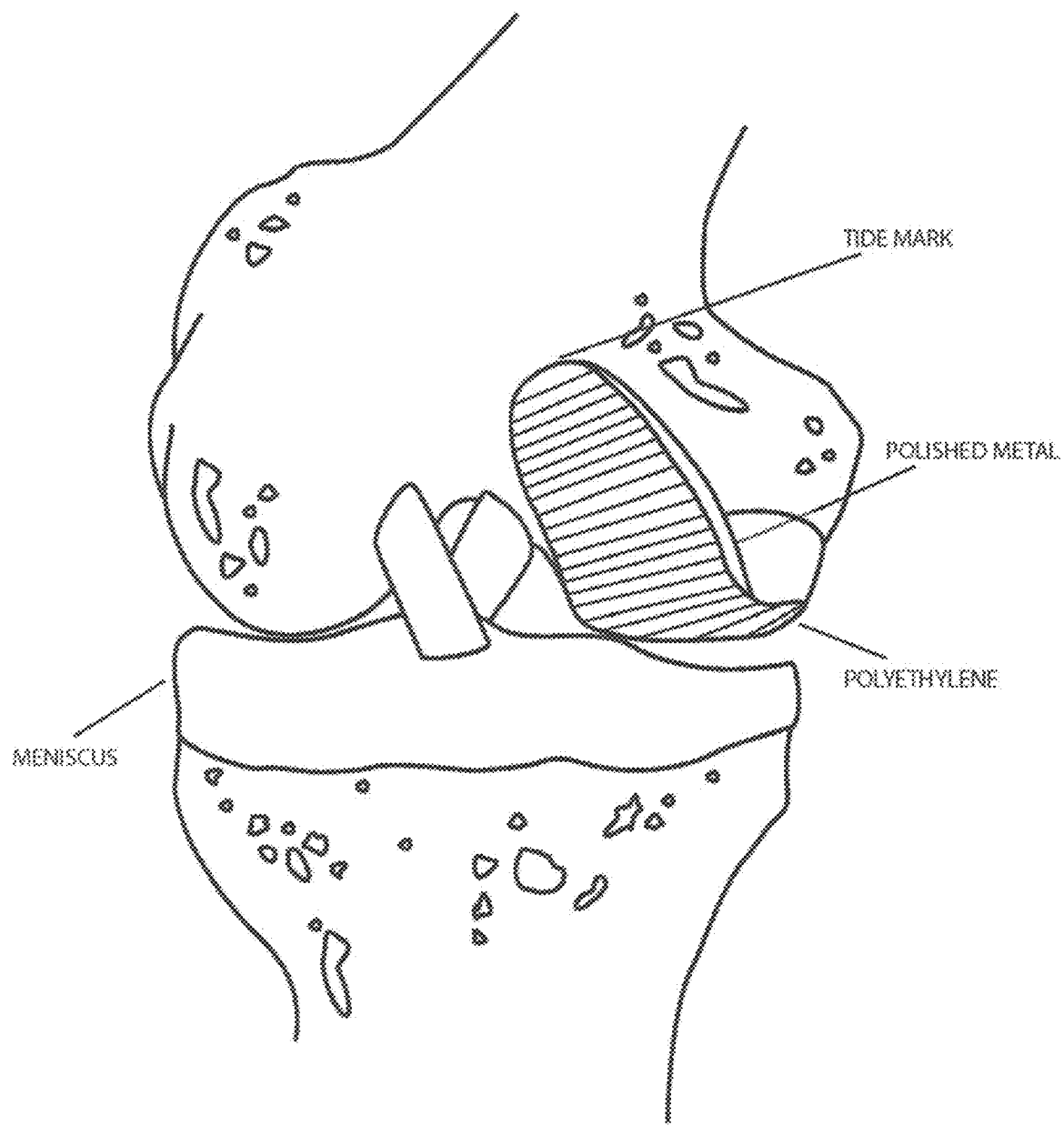
FIG. 11 is a schematic diagram illustrating the two-piece distal femoral condyle replacement implanted into the knee.

FIG. 11 is a schematic diagram illustrating the distal femoral condyle replacement component comprising the metal backed component used with the polyethylene component and being cemented into the femur bone.

Figure 12:
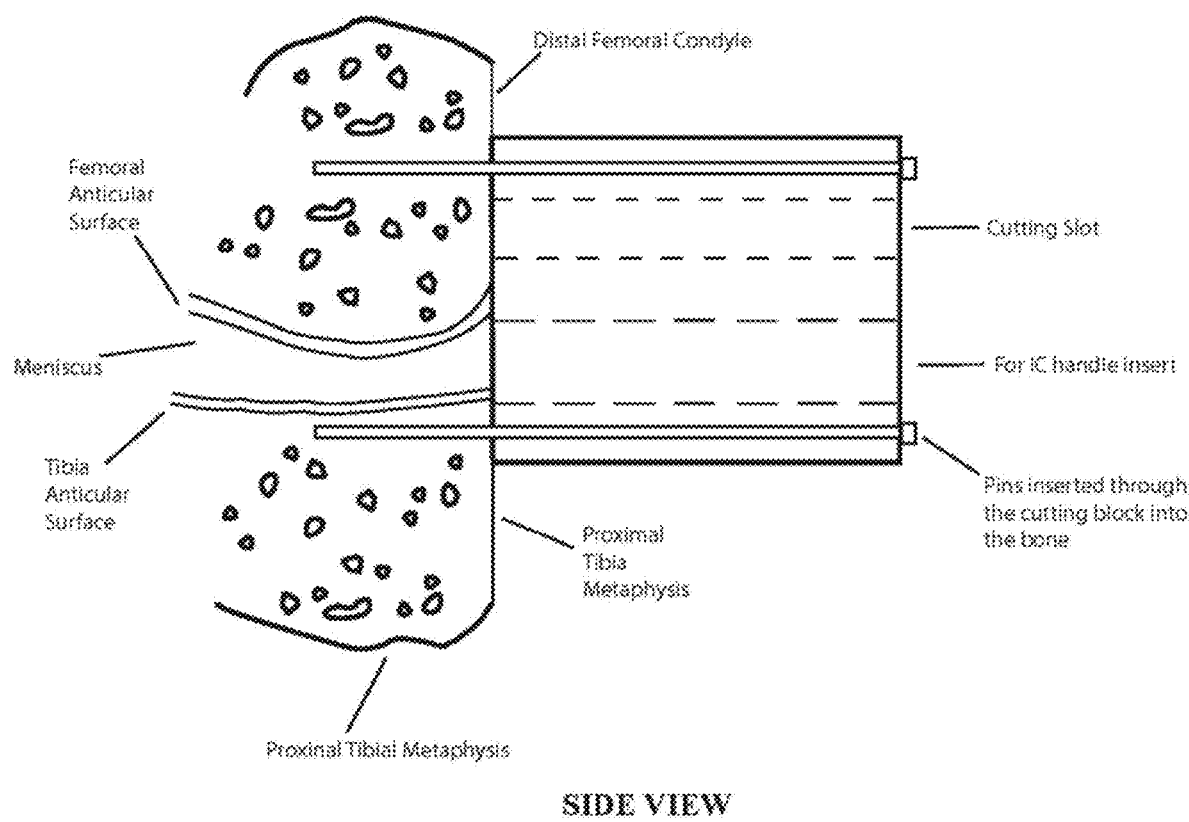
FIG. 12 a schematic diagram illustrating a side view of the knee with the cutting block pinned in place.

FIG. 12 a schematic diagram illustrating a side view of the knee joint prior to the distal femoral condyle replacement, and illustrating the cutting block pinned in place. Having the pins in both the distal femur and proximal tibia allows the surgeon to make the distal femoral condyle cut either with the knee flexed or extended. If the surgeon choses to make the bone cut in extension, having pins on both sides of the joint will allow a more stable cut. Once the cut is made, either partially or fully, the tibial pins may be removed and the knee flexed to inspect the cut. However, the surgeon may choose to insert only the femoral pins, flex the knee, and then make the distal femoral condylar bone cut.

The various steps and components discussed with respect to FIG. 1 are described in further detail below.

Pre-Operative Planning

As with any contemplated joint replacement, it is important that a comprehensive history pertaining to the patient's knee is obtained and a detailed physical exam of the knee is performed. Plain radiographs and an MRI need to be carefully evaluated. When considering a FCRA, there are important parameters to consider. No single one is absolutely definitive. These all need to be considered and discussed with the patient so he or she is involved in the decision making process (the art of medicine).

History

Where is the patient's pain located? If primarily around the involved compartment, an indication that FCRA may be indicated. If more diffuse and widespread, a FCRA may not be indicated.

When does it bother the patient? If primarily with weight bearing and/or going upstairs, more indicative of single compartment damage. If significantly present even without weight bearing, and when going downstairs, the damage may be more widespread and involve the patella and trochlea surfaces.

Does the knee give out with twisting activities? More likely damage to the weight bearing surface. Of course, there could be a localized meniscus tear without damage. Diagnostic testing will help determine this.

Physical Examination

Is there a deformity with weight bearing; genu *varus* with damage to the medical compartment, genu valgus with damage to the lateral compartment? Is there observed instability with ambulation? If so, these are a contraindication to a FCRA.

Is the pain confined to one compartment with palpation? The presence of pain to palpation to multiple compartments could indicate that there is more than one compartment damaged.

Is there substantial loss of range of motion? A loss of more than five degrees of full extension or flexion less than 125 is a relative contraindication for FCRA.

Is there ligamentous laxity? Mild apparent medial or lateral laxity is to be expected when a mild genu *varus* or genu valgus deformity is present. Substantial medial or lateral laxity, or anterior or posterior laxity, is contraindications to FCRA.

Are pain, crepitation, and mechanical findings confined to one weight bearing compartment with meniscal testing? If more than one compartment is involved, this may indicate that the FCRA is not appropriate, or there are bi-compartmental meniscus tears.

Plain Radiographs

A minimum of four views should be obtained: standing AP, standing PA, lateral, and the patellar trochlear view of the surgeon's choice (e.g. Houghston, sunrise, etc.).

The angle between the femur and tibia on the standing AP will need to be measured. While this can be measured on the computer screen of the electronic views, it is recommended that hard copies be obtained on any patient that FCRA is being considered. This will allow more accurate measurement be made to determine genu *varus* and genu valgus. A *varus* angle greater than five and a valgus angle greater than 8 is a relative contraindication to FCRA, as it suggests that instability may be present. If the contralateral knee is normal, that knee should be measured and compared to the knee being considered for FCRA.

The amount of narrowing and subchondral sclerosis needs to be determined on the standing radiographs. Both the standing AP and PA need to be evaluated to assure that only one of the weight bearing compartments is damaged. Narrowing, the genu angle, subchondral cysts, and subchondral sclerosis are all important to consider.

There are two specific areas to consider on the lateral view. The first is to determine if there are osteophytes at the superior and inferior pole of the patella, and the superior trochlea. If substantial, these osteophytes would indicate that there is patella trochlear damage and may be a contraindication to FCRA. The second is to review the posterior condyle of the compartment being considered. The presence of osteophytes, subchondral cysts, and subchondral sclerosis would indicate that a traditional unicompartmental may be necessary.

The patella-trochlear view will need to be examined for two findings. The first is for substantial signs of degeneration: osteophytes, narrowing, subchondral cysts, and subchondral sclerosis. If substantial, the patient may require a total knee replacement. The second is for lateral patella tilt or subluxation. If the unicompartmental arthroplasty being considered is medial, and if a genu *varus* deformity is overcorrected, this may lead to increased patella trochlear instability and degeneration, causing rapid failure and necessitating revision to a total knee.

After careful consideration of the patient's history, physical examination, and review of plain radiographs, a determination should be made if the patient is a possible candidate for FCRA. If the patient is determined to be a candidate, than an MRI should be obtained. (FIG. 1, Step 1A) There are six areas that specifically need to be scrutinized:

The patella and trochlea: The integrity of the subchondral bone and hyaline cartilage of each need to be determined. Substantial damage to either or both, especially when correlated with findings on the history and physical, would indicate a total knee or bicompartmental arthroplasty is indicated.

The opposite compartment: The integrity of the subchondral bone, the hyaline cartilage, and the meniscus need to be determined. If there is no significant damage to the compartment, yet the meniscus is torn, an arthroscopic meniscectomy on the opposite compartment will need to be performed at the same time as the FCRA.

The distal femoral condyle and underlying hyaline cartilage: Damage needs to be determined and confirmed.

The posterior femoral condyle and underlying hyaline cartilage: If not damaged, the distal femoral FCRA may be indicated. If substantial damage, than both the distal and posterior condyle will need replacement.

The meniscus of the involved compartment: If torn, than either arthroscopic or open partial meniscectomy will need to be performed at the time of the FCRA. (FIG. 1, Step 2).

Tibial plateau and overlying hyaline cartilage: If normal, than a FCRA could be indicated, after considering the history, the physical examination, review of the plain radiographs, and MRI.

Instrumentation

Intra-compartmental Insert (IC Insert): This has a curvilinear, pliable plastic surface that will be used for the FCRA procedure. The pliable plastic surface will not cause any damage to tibial articular surface, as opposed to a metal insert. It is 1.5 cm wide. The curvilinear plastic component will be placed in between the tibial and femoral articular surfaces, over the anterior meniscus. The handle of the IC Insert will be hard plastic or metal and will contain a hole for placement of the external alignment guide, if the surgeon's preference is such. (FIGS. 3A-3B).

External Alignment guide: If used, this will be inserted through the handle of the IC insert to check for AP and lateral alignment prior to fixation of the distal femoral cutting block to the proximal tibia, if the surgeon feels it is necessary to check this.

Distal femoral cutting block: This block will be attached to the IC Insert. Preferably, there will be neutral cutting slot. By slight angulation of the cutting block, e.g., 1 degree, 2 degree, or 3 degree superior slope, more or less of the distal condyle can be removed. This will allow a slight increased coverage if the distal femoral condyle wear extends slightly into the posterior condyle. However, unless otherwise determined, a neutral cut should be made. (FIGS. 4A-4B).

Figure 4C:
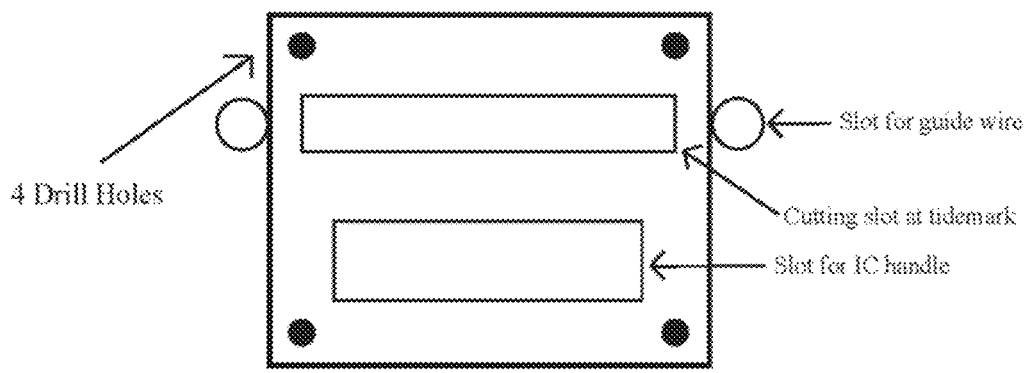
FIG. 4C is a schematic diagram depicting a front view of an alternate cutting block used in the method(s) and system(s) of present disclosure.
Figure 4D:
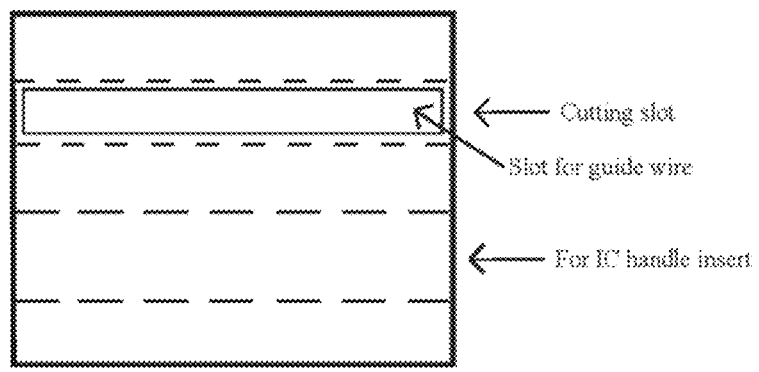
FIG. 4D is a schematic diagram depicting a side view of the alternate cutting block of FIG. 4C.
Figure 6:
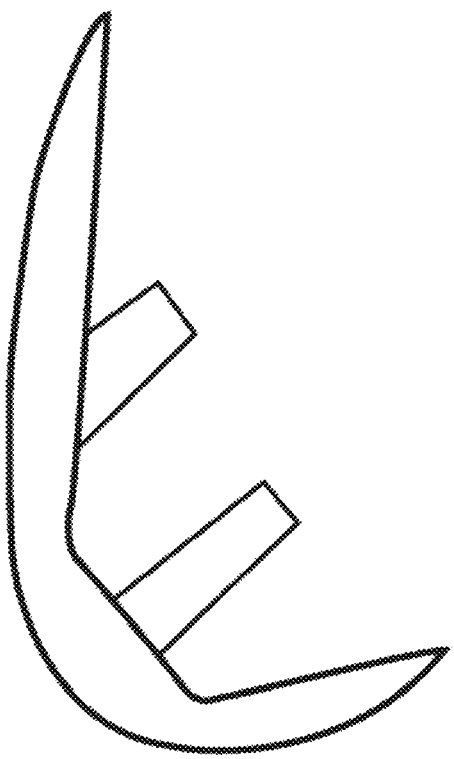
FIG. 6 is a schematic diagram of a distal and posterior femoral condyle trial.

Alternate distal femoral cutting block: This block will be attached to the IC Insert through the slot for the IC Handle. On each side of the block at the level of the cutting slot is a slot, preferably a round slot, for placement of a guidewire. This guidewire will be placed against the bone of the femoral condyle to be cut. The surgeon will use this to assure the proper distal femoral cut. One of the unique functions and advantages due to the flexibility imparted by the plastic material of the IC Insert is that once the femoral cutting block is place over the IC Insert handle, the surgeon is able to change the position of the femoral cutting block once aligned with the guide wire placed in its slot. This assures the correct distal femoral cut. The distal femoral cutting block is then pinned into place prior to making the distal femoral cut. (FIGS. 4C-4D).

FCRA (Box) retractor This is a retractor designed specifically for the FCRA procedure. Since the incision only needs to expose the most inferior aspect of the distal femur and most superior aspect of the tibia, it may be relatively small. However, the patella, the patellar and quadriceps tendon, and the opposite capsular structures must be retracted to allow placement of the instruments and allow visualization of the bone cuts, trial sizing, and then placement of the definitive component. There are four right angle blades (two for medial structures and two for lateral structures), which may be either metal or hard plastic (if necessary to place the retractor under the patella itself). The blades come in two depths, shallow and deep. The metal lattice support is movable superior/inferior and medial/lateral to allow for adequate exposure. This also keeps the retractor in place while flexing and extending the knee while assessing the component. (FIG. 2A-2C).

Components

Finite Element Analysis defines the function of the knee to be one of various contact points between structures of different mesh densities. (Pfeiffer, F. M., Volume 29, Number 2, 2106, *The Journal of Knee Surgery*.) The knee weight bearing areas consist of three structures of different densities, bone (rigid, the distal femur and proximal tibia), hyaline cartilage (semi-rigid, the femoral and tibial articular surfaces) and the meniscus (soft, the medial and lateral meniscus).

Traditional Uni-compartment and total knee replacement has evolved so that a rigid surface (the femoral component) articulates with a semi-rigid surface (the polyethylene) liner of the tibia and the polyethylene patella component). This has worked well over the years and remains the mainstay of knee replacement arthroplasty.

However, observed during arthroscopic surgery on the knee, often times there exists a partial meniscus tear, which in turn has damaged substantially the corresponding gliding surface of the distal and/or posterior femoral hyaline cartilage, while leaving the tibial hyaline cartilage normal. Currently, arthroscopic debridement of the damaged femoral articular surface and removal of the torn meniscus is all that can be offered from a mechanical standpoint to help these patients. Hyaluronidase injections, anti-inflammatory medications, knee supports, and orthotics can sometimes help these patients. Commonly, the compartment involved in these patients quickly deteriorates to where a Uni-compartment arthroplasty becomes necessary.

Since the tibial articular surface is essentially undamaged and much of the meniscus remains intact, the basic geometry of the compartment is normal, except for the damage to the femoral gliding surface. Accordingly, the presently disclosed method(s) would not replace the entire compartment. The presently disclosed method(s) would just replace the damaged distal femoral hyaline surface, while leaving the tibial articular surface and undamaged meniscal tissue intact.

Since the hyaline cartilage surface is a semi-rigid surface, replacing it with a rigid surface (the current metal surfaces being used) would be expected to cause progressive damage to the tibial hyaline surface. It would be more physiologically compatible to replace it with a less rigid surface. That way, the semi-rigid against semi-rigid surface of the normal hyaline cartilage would be preserved. The "plastic deformation" that occurs in the femoral articular surface at the junction of trochlea and the distal femoral condyle, is the so called "tide-mark." These are semi-rigid surfaces, not rigid surfaces.

Currently, with today's materials, the replacement of the distal femoral condyle should be a polyethylene component. That way, two semi-rigid surfaces would be articulating (i.e. polyethylene femoral condyle and native tibial hyaline cartilage), rather than a semi-rigid surface (native tibial hyaline cartilage) against a rigid surface (metal distal femoral component). However, laboratory testing can aid in the determination of the most appropriate surface for replacing the distal or distal/posterior femoral condylar surface.

There are three embodiments for the femoral condyle replacement, whether the distal femoral condyle or both the distal and posterior femoral condyles. Preferably a polyethylene component with at least two pegs for cement fixation into the femur is used. A second, alternative component will be a metal back component with at least two pegs cemented into the femur with snap on polyethylene liners of various thicknesses. The third embodiment is a metal component with at least two pegs cemented into the distal femur.

FCRA Surgical Technique

An arthroscopic procedure may first be performed. If necessary, a partial meniscectomy will need to be performed. (FIG. 1, step 2). It is unusual that there will be a significant amount of damage to the distal femoral condyle to warrant a FCRA without meniscal tearing. Whether performed arthroscopically or as part of the open procedure, the remaining meniscus need to be well-balanced and stable, especially posteriorly. Steps 1A and 2 may previously have been performed by an Arthroscopist who refers the patient for the FCRA. (FIG. 1, Step 1B).

If an arthroscopy is performed first, arthroscopic portal on the side having the open procedure may be vertical, and closer to the midline than what the surgeon is used to. This will allow the arthroscopic incision to be incorporated into the open procedure. Of course, this depends on where the surgeon normally makes his or her portal. However, if the surgeon prefers a horizontal incision, made slightly medially or laterally to the midline, that is very acceptable.

After a decision to proceed with the FCRA is made (FIG. 1, Step 3), a small vertical arthrotomy incision (which would be approximately 2-3 inches) is made slightly medially or laterally to the patellar tendon, depending on what compartment is involved. (FIG. 1, step 4) The box retractor is positioned (FIGS. 2A-2C). As with any surgical technique, the incision needs to be long enough to allow adequate visualization. Initially, it is recommended that the incision be made longer, and then may be shortened as the surgeon gains confidence in the procedure.

The "tide mark" is checked and marked with the knee in its full extension. With the knee remaining in extension, a slight valgus stress (for medial compartment) or *varus* stress (for lateral compartment) is imparted and the pliable plastic portion of the IC insert (FIGS. 3A-3B) is then inserted over the anterior third of the meniscus in between the distal femoral condyle and tibial plateau. (FIG. 1, Step 5). The anterior meniscus usually sits slightly inferior to the medial tibial articular surface and is pliable enough to normally allow the IC Insert to be placed into the medial compartment without difficulty. In unusual cases where the IC Insert cannot be placed over the anterior meniscus, the anterior meniscus can be incised at this time and repaired at the end of the case.

The femoral cutting block (FIGS. 4A-4B) is attached to the IC Insert, making sure the cutting slot aligns with the tide mark, and is then affixed with two pins into the distal femur. (FIG. 1, Step 6) If surgeon preference, the external alignment guide is then inserted through the metal handle of the IC Insert and the AP, lateral, and rotational planes are checked. It is important not to place the IC Insert against the tibial spine, as this will cause external rotation of the cutting blocks. However, since the tibial articular surface is not being resected, rotation of the implanted femoral component will be determined prior to cementing. The external alignment guide may not be necessary.

Once alignment and rotation is confirmed, the distal femoral cutting block is pinned to the tibia. This allows secure fixation. The distal femoral is then cut. (FIG. 1, Step 7) If the posterior condyle is also to be removed, the surgeon will use his or her standard system for the posterior and chamfer cuts. (FIG. 1, Steps 8B and 10).

All the instrumentation is now removed. The trial components are tried until the proper size is determined. (FIGS. 5A-5C and 5D or 6). It is important that trial component is not proud either anterior or posterior, but rather are recessed. If proud anteriorly, this can cause impingement on the patella. If proud posteriorly, this can cause impingement on the posterior meniscus (if saved, or on the posterior tibial articular surface if not. The knee is put through a ROM to make sure there is not impingement anteriorly or posteriorly.

The fixation posts are then drilled after confirmation of proper size, motion, and setting of the trial is confirmed. (FIG. 1, Step 9 or 10). The distal femoral component (FIG. 1, Step 9; and FIG. 5D) or the distal and posterior femoral condyle trial (FIG. 1, Step 10; and FIG. 6) is then cemented into place. Excess cement is removed after the cement hardens. Again, a check is made to assure no impingement.

The knee is irrigated, tourniquet released if used, and hemostasis obtained. The surgeon will need to determine if a drain is necessary. No immobilization is required unless preferred by the surgeon.

This process is amendable to the use of computer generation of the components. When the surgeon and patient have decided that this method of treatment may be appropriate, the surgeon can submit the patient's MRI results for computer analysis. A computer and software can evaluate the MRI results to confirm whether or not the patient is a candidate for the FCRA based upon an analysis of the data. The computer analysis will determine the need for a FCRA. First, by use of the MRI, a tear of the meniscus will be determined, if present or not. Secondly, the MRI computer analysis will determine if there is any damage to the tibial articular surface. If there is, the patient is not a candidate for a FCRA. Thirdly, the MRI computer analysis will determine the extent of the femoral articular damage; the depth, the location and size. If significant damage is present, the computer can generate a design of a combined Intracondylar insert/distal femoral cutting block, and also a design of an implantable component. If both distal and posterior femoral condyles are to be replaced, the surgeon will use the MRI computer generated combined Intracondylar insert/distal femoral cutting block for the initial cut. The chamfer/posterior cuts would then be made.

Upon confirmation that the patient is a candidate for the FRCA, the one piece, patient-specific design of a combination of the Intra-condylar insert and distal femoral cutting block can be generated by the computer and software based on the patient's MRI data, appropriate for the size, shape and location relative to the patient's specific knee structure. This will be fabricated of a composite material that will not cause any damage to the tibial articular hyaline cartilage surface. A trial component can also be included with the patient specific cutting block and implantable component.

This one piece Intracondylar insert/distal femoral cutting block component will then be use in the surgical procedure. FIG. 7A illustrates a side view of the combined, one-piece Intra-condylar insert and distal femoral cutting block. FIG. 7B is a front view of the combined, one-piece Intra-condylar insert and distal femoral cutting block.

Also included will be the definitive, patient specific component to be implanted, the design of which is also generated by the computer and software from the patient's MRI data, appropriate for the size, shape and location relative to the patient's specific knee structure, whether distal femoral condyle or combination of distal and posterior femoral condyle.

After the arthroscopic aspect of the procedure, at the time of the FCRA surgery, the surgeon will place the patient-specific intra-condylar insert between the distal femoral condyle and tibial articular surface, pin the attached cutting block in place, make the distal femoral cut (and posterior and chamfer cuts if the both distal and posterior condyles are to be replaced), check the trial component, and then cement in the implant included.

While the embodiment(s) disclosed herein are illustrative of the structure, function and operation of the exemplary method(s), system(s), component(s) and device(s), it should be understood that various modifications may be made thereto with departing from the teachings herein. Further, the components of the method(s), system(s), component(s) and device(s) disclosed herein can take any suitable form, including any suitable components capable of adequately performing their respective intended functions, as may be known in the art.

While the foregoing discussion presents the teachings in an exemplary fashion with respect to the disclosed method(s), system(s), component(s) and device(s) for femoral condylar resection arthroplasty of the knee, it will be apparent to those skilled in the art that the present disclosure may apply to other arthroscopic and/or arthroplasty surgical method(s) and system(s). Further, while the foregoing has described what are considered to be the best mode and/or other examples, it is understood that various modifications may be made therein and that the subject matter disclosed herein may be implemented in various forms and examples, and that the method(s), system(s), component(s) and device(s) may be applied in numerous applications, only some of which have been described herein.

What is claimed is:

1. A method for a medial or lateral unicondylar femoral condylar resection arthroplasty of the knee, comprising the steps of:
   preserving undamaged meniscus in the knee via arthroscopy or arthrotomy;
   making an incision over a joint line of the knee;
   placing an intercondylar insert between articular surfaces of a distal femoral condyle and a tibial plateau with the knee in extension;
   pinning a distal femoral condyle cutting block at a tide mark;
   resecting the distal femoral condyle;
   using a posterior and chamfer cutting block;
   resecting the posterior femoral condyle;
   sizing the distal and posterior femoral condyle with trial components; and
   replacing the distal and posterior medial or lateral femoral condyle with a correspondingly sized two-piece distal and posterior femoral condyle component.

2. The method of claim 1, wherein the two piece distal and posterior medial or lateral femoral condyle component comprises a polyethylene piece and a metal piece.

3. The method of claim 2, wherein the step of replacing the distal and posterior medial or lateral femoral condyle with a correspondingly sized two-piece distal and posterior femoral condyle component further comprises attaching the metal piece and the polyethylene piece via tongues and grooves.

* * * * *